United States Patent
Wolf, Jr. et al.

(10) Patent No.: US 9,453,834 B2
(45) Date of Patent: Sep. 27, 2016

(54) METHOD OF COMPRESSING FUEL CELL ELECTRODES, RESULTANT FUEL CELL, AND A HOUSING FOR THE FUEL CELL WHICH UTILIZES ELECTROLYTE RESERVOIRS

(71) Applicant: Alcotek, Inc., St. Louis, MO (US)

(72) Inventors: Karl R. Wolf, Jr., Eureka, MO (US); Joe Fodor, Fenton, MO (US)

(73) Assignee: Alcotek, Inc., St. Louis, MO (US)

( * ) Notice: Subject to any disclaimer, the term of this patent is extended or adjusted under 35 U.S.C. 154(b) by 144 days.

(21) Appl. No.: 14/444,448

(22) Filed: Jul. 28, 2014

(65) Prior Publication Data

US 2015/0027884 A1     Jan. 29, 2015

Related U.S. Application Data

(60) Provisional application No. 61/858,955, filed on Jul. 26, 2013.

(51) Int. Cl.
*G01N 33/497* (2006.01)
*G01N 27/404* (2006.01)

(52) U.S. Cl.
CPC ...... *G01N 33/4972* (2013.01); *G01N 27/4045* (2013.01); *Y10T 29/49108* (2015.01)

(58) Field of Classification Search
CPC ..... G01N 33/49; G01N 33/98; G01N 27/237
IPC .................................................. G01N 33/49
See application file for complete search history.

(56) References Cited

U.S. PATENT DOCUMENTS

| | | | |
|---|---|---|---|
| 4,035,551 A | 7/1977 | Grevstad | |
| 5,302,274 A | 4/1994 | Tomantschger et al. | |
| 5,395,507 A | 3/1995 | Aston et al. | |
| 5,830,337 A | 11/1998 | Xu | |
| 5,980,709 A * | 11/1999 | Hodges et al. | 204/403.06 |
| 5,985,675 A * | 11/1999 | Charm et al. | 436/514 |
| 7,022,213 B1 | 4/2006 | Austen et al. | |
| 7,534,333 B2 | 5/2009 | Khalafpour et al. | |
| 2006/0142651 A1 * | 6/2006 | Brister et al. | 600/347 |
| 2007/0072048 A1 | 3/2007 | Hongo et al. | |
| 2007/0154765 A1 | 7/2007 | Bayer et al. | |
| 2009/0194417 A1 | 8/2009 | King | |
| 2010/0190089 A1 | 7/2010 | Akiyama | |
| 2013/0101919 A1 | 4/2013 | Hiraiwa et al. | |

OTHER PUBLICATIONS

International Search Report, International Patent Application No. PCT/US2014/048445, mailed on Nov. 7, 2014, 11 pages.

* cited by examiner

*Primary Examiner* — Jennifer Dieterle
(74) *Attorney, Agent, or Firm* — Lewis Rice LLC

(57) ABSTRACT

An electrode element and fuel cell and a new method of manufacturing a fuel cell, particularly for use in a breath alcohol detector. This new element includes a reservoir for extra electrolyte that can allow near perfect capillary action to keep the electrode substrate full of electrolyte for long periods of time, increasing its useful life, especially under harsh conditions. Further, the capillary action need not work through a layer of electrode and can be integrally formed with the electrode element to eliminate or reduce loss due to connective surfaces. Wire connections and arrangements are generally of no concern in this design as the reservoirs for electrolyte connect directly to the substrate and electrolyte does not need to pass through an electrode.

15 Claims, 6 Drawing Sheets

METHOD OF COMPRESSING FUEL CELL ELECTRODES, RESULTANT FUEL CELL, AND A HOUSING FOR THE FUEL CELL WHICH UTILIZES ELECTROLYTE RESERVOIRS

CROSS REFERENCE TO RELATED APPLICATION(S)

This application claims benefit of U.S. Provisional Patent Application Ser. No. 61/858,955, filed Jul. 26, 2013, the entire disclosure of which is herein incorporated by reference.

BACKGROUND

1. Field of the Invention

Described herein is a fuel cell that includes a reservoir for electrolyte. Specifically, the fuel cell may include one or more "sponge reservoirs" which comprise a portion of the porous substrate which is uncompressed and in fluid communication (and generally integrally formed) with the substrate which is compressed between the electrodes.

2. Description of the Related Art

For the purposes of public safety on the roads and elsewhere, there is a need to make sure that individuals are not operating potentially dangerous machines (such as automobiles) while they are impaired by the effects of alcohol consumption. To try and prevent people from driving drunk, most states have enacted laws that impose fines or other criminal penalties if individuals have a breath or blood alcohol level above a certain amount. In order to effectively enforce these laws, it is necessary to be able to measure the alcohol concentration in human breath and compare the results against legal limits. There are a variety of measuring instruments used for determining the concentration of alcohol in human breath ranging from small hand held devices to larger bench top units and machines built into cars or certain machinery. Since a determination of breath alcohol above the legal threshold can result in criminal penalties, loss of a job, or other sanctions, the accuracy of these instruments is paramount.

Fuel cells which are being used as sensors, and particularly fuel cells as alcohol sensors such as may be used in breath alcohol sensors, have typically had the active element constructed as shown in FIG. 1. This assembly (100) is typically manufactured by arranging the components and then compressing the assembly (100) under pressure in order to get the material of the electrodes (101), generally platinum, to adhere to the substrate (103). In the process, the porous substrate (103) is typically permanently deformed resulting in a smaller effective pore size of the substrate compared to its pore size prior to pressing. It is these pores of the substrate (103) that hold liquid electrolyte to allow the fuel cell (100) to function and the pores are typically filled by soaking the assembly (100) after pressing. Once filled with liquid electrolyte, the active element (100) can act as a fuel cell.

Typical electrode assemblies might be round or square as shown in FIG. 2 and are typically less than 1 mm thick. Substrates (103) are generally a porous material such as, but not limited to, porous PVC and porous polypropylene, but there are many candidate materials. Those skilled in the art will understand that these assemblies (100) are, therefore, generally very small and therefore typically will hold a very small amount of electrolyte. Five one-hundredths (0.05) of a milliliter would not be an unusual quantity.

Fuel cell sensors in portable equipment, such as those used by highway patrol officers, by definition, must operate in a variety of ambient conditions such as hot, cold, humid, and arid environments. Hot and/or arid conditions tend to draw water out of the fuel cell electrolyte as the water in the electrolyte tries to reach equilibrium with the environment. Even if the electrode assembly (100) is enclosed in a case (300), water can be drawn out through the case material, which is rarely completely air and fluid sealed, or through necessary sampling ports (301) allowing the fuel cell (100) to be used in the breath alcohol sensor as is shown in FIG. 3. Previously attempted remedies against water loss generally add cost and complexity and are not 100% effective, especially over an expected sensor life in the marketplace measured in years, and especially in a punishing environment.

In some cases, fuel cells (100) are used in indoor bench top equipment. Although this is typically a moderated environment compared to the great outdoors, indoor conditions can still be quite arid, especially in winter. Fuel cells (100) are also often heated in bench top equipment for measuring reasons, generally making the fuel cell microenvironment even drier than the overall room conditions.

Those skilled in the art will understand that if all the water, or nearly all the water, is drawn out of a fuel cell (100) electrolyte, the fuel cell (100) will cease to work and may become permanently damaged. Various degrees of water loss short of 100%, or nearly 100%, typically do not keep a fuel cell (100) from measuring accurately. However, the response time may become slower, for example.

Over the years, a variety of methods have been used to deal with electrolyte water loss. In one example where the gas sample is human breath (which is common in a breath alcohol detector), every time a sample is taken, moisture will be added to the substrate (103) from humidity in the breath as shown in FIG. 4. However, the amount of moisture added per sample is generally so small, and the typical number of tests run on an instrument over a year is also small enough that these additive effects are typically swamped by the opposite effect of water loss.

Humid ambient conditions (which result in less water loss and possibly even water gain through the inverse of the above processes) are more likely to be the driving force behind water gain in a fuel cell than breath addition. A fuel cell sensor (100) containing an electrolyte can take on water from very humid ambient conditions. The paths of water gain from the ambient are the same as water loss to the ambient, only in reverse. Those skilled in the art will understand that, while this can be beneficial, if the sensor substrate (103) is already saturated with liquid, it may continue to take on liquid from the humid ambient conditions until the volume of such liquid exceeds the designed containment capacity of the sensor (100). In this case, liquid can overflow the sensor (100) and appear on the electrode (101) surfaces or other locations where it will likely hinder the intended operation of the sensor (100).

Certain fuel cell designs have allowed manufacturers to experiment with manually adding drops of water directly to an exposed electrode (101) (anode) of the fuel cell (100) when it has dried out significantly as shown in FIG. 5. Results have been mixed as water loss often causes the cell (100) to reach a tipping point where adding water back does not reverse the effects of losing it in the first place. Further, at times the drier platinum electrode (101) becomes partially hydrophobic and the added liquid can take considerable time to soak in, if it can at all. Thus, addition via the anode side of the fuel cell (100) is often ineffective.

It is generally believed that the ideal electrolyte situation is to constantly keep the substrate (103) filled from the very beginning of the fuel cell's (100) useful life. For many years, some fuel cell sensor (100) manufacturers have been adding "backup" disks (107) in the construction of fuel cell sensor (100) assemblies. This is an extra disk of substrate without an attached electrode that is typically assembled behind the cathode (101). The backup disk (107) has typically been made of the same substrate material as the electrode disk (103), but without any compression, leaving the pores in their original state. Therefore, this disk (107) will hold more electrolyte than the pressed version.

The backup disk (107) acts as a reservoir for extra electrolyte to replenish the electrolyte in the substrate (103) between the electrodes (101) when water is lost to ambient conditions. The smaller (compressed) pores of the substrate (103) between the electrodes (101) preferentially stays full compared to the backup disk (107) due to capillary action since the backup disk (107) pores are larger. FIG. 6 provides an embodiment of such a backup disk (107).

This solution has worked reasonably well in the field in many instances. There are a couple of drawbacks with this construction, however. The complete fuel cell sensor assembly (100) generally includes wires (111) to connect the electrode (101) surfaces to an external circuit (109) for measuring the current produced from a gas sample. This construction typically places a wire (111) between one electrode surface (101) and the backup disk (107) which to some degree prevents a perfect contact surface between electrode (101) and backup disk (107) as shown in FIG. 7. Thus, the capillary action is somewhat hindered between the backup disk (107) and the substrate (103). Also, as mentioned above, the electrode (101) surface itself presents an additional layer through which the moisture must travel and may detract from an ideal capillary action.

As a final note, there is no good way to tell whether a fuel cell (100) is flush with electrolyte or starved for electrolyte unless or until a large degradation in performance becomes apparent. By the time this happens, it is often too late to reverse that degradation by adding water or electrolyte and the fuel cell (100) is effectively destroyed.

SUMMARY

The following is a summary of the invention in order to provide a basic understanding of some aspects of the invention. This summary is not intended to identify key or critical elements of the invention or to delineate the scope of the invention. The sole purpose of this section is to present some concepts of the invention in a simplified form as a prelude to the more detailed description that is presented later.

Because of these and other problems in the art, described herein is a fuel cell that includes a reservoir for electrolyte. Specifically, the fuel cell may include one or more "sponge reservoirs" which comprise a portion of the porous substrate which is uncompressed and in fluid communication (and generally integrally formed) with a portion of the substrate which is compressed between the electrodes. The fuel cell may also include one or more liquid reservoirs in fluid communication with the sponge reservoirs. The fuel cell is generally constructed with a continuous substrate that extends beyond the periphery of the electrodes and the electrodes are compressed into a portion of the substrate, but not all the substrate. This creates two sections of substrate. The first compressed portion along with the attached electrodes forms the active element of the fuel cell and the second uncompressed section is a sponge reservoir for providing additional electrolyte to the first portion.

There is described herein, among other things, a fuel cell comprising: at least two electrodes; and a porous substrate, said substrate comprising a compressed portion and an uncompressed portion which are integrally formed and in fluid communication with each other; wherein a first of said at least two electrodes is arranged on a first side of said compressed portion of said porous substrate; and wherein a second of said at least two electrodes is arranged on a second side of said compressed portion of said porous substrate.

In an embodiment, the fuel cell further comprises an encapsulating housing.

In an embodiment of the fuel cell, the housing includes at least one liquid reservoir in fluid communication with said uncompressed portion of said porous substrate.

In an embodiment of the fuel cell, the at least one liquid reservoir comprises at least three liquid reservoirs, said at least three liquid reservoirs being positioned so that liquid in at least one of said at least three reservoirs contacts said uncompressed portion of said porous substrate regardless of orientation of said fuel cell.

In an embodiment of the fuel cell, the electrodes comprise platinum.

In an embodiment of the fuel cell, the fuel cell is used in a breath alcohol sensor.

In an embodiment of the fuel cell, the porous substrate comprises porous polypropylene.

In an embodiment of the fuel cell, the porous substrate comprises porous polyvinylchloride (PVC).

In an embodiment of the fuel cell, the pores in said porous substrate include a liquid electrolyte.

In an embodiment of the fuel cell, the at least two electrodes are smaller than said substrate.

In an embodiment of the fuel cell, the electrodes are circular.

In an embodiment of the fuel cell, the substrate is polygonal.

In an embodiment of the fuel cell, the compressed substrate includes a megapore.

In an embodiment of the fuel cell, the uncompressed substrate includes a megapore.

There is also described herein, in an embodiment, a method of forming a fuel cell, the method comprising: placing a first electrode on a first side of a substrate, said first electrode covering only a portion of said first side; placing a second electrode on a second opposing side of a substrate, said second electrode covering only a portion of said second side; moving said first electrode and said second electrode toward each other so as to compress said substrate located between said first electrode and said second electrode while not compressing said substrate not located between said first electrode and said second electrode.

In an embodiment of the method, the moving of the first and second electrodes toward each other comprises moving both said first electrode and said second electrode.

In an embodiment of the method, the moving of the first and second electrodes toward each other comprises moving only one of said first electrode and said second electrode.

DESCRIPTION OF THE PREFERRED EMBODIMENT(S)

Because of these and other problems in the art, described herein is a new design of an electrode element and fuel cell and a new method of manufacturing a fuel cell. This new element includes a reservoir for extra electrolyte that can allow near perfect capillary action to keep the electrode substrate full of electrolyte for long periods of time. This can increase its useful life, especially under harsh conditions.

Further, the capillary action need not work through a layer of electrode and can be integrally formed with the electrode element to eliminate or reduce loss due to connective surfaces. Wire connections and arrangements are generally of no concern in this design as the reservoirs for electrolyte connect directly to the substrate and electrolyte does not need to pass through an electrode.

FIGS. 8-11 provide an embodiment of a fuel cell (200) which utilizes a selective compression of the substrate (203) to form an active element (403) and a sponge reservoir (603). As can be seen in the FIGS, the fuel cell (200) will generally utilize a single piece of substrate material, in this embodiment an about 25 mm square of a porous material such as, but not limited to, porous PVC or porous polypropylene, which is selectively compressed at only a portion of its surface to form two portions which are integrally connected. While the exact type of substrate (203) is not critical, it must be porous and will generally be composed of traditional materials. The exact type of electrolyte used is also not critical, but the electrolyte will generally be liquid or in suspension or solution.

Figure 8:
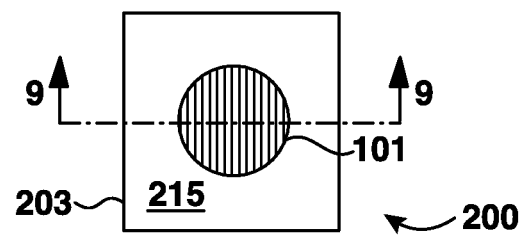
FIG. 8 provides a planar top view of a substrate with selectively applied electrodes in the center.
Figure 9:
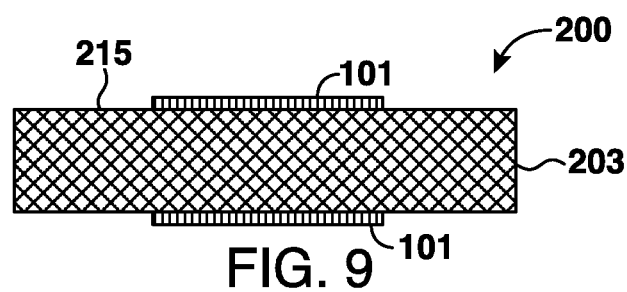
FIG. 9 provides an enlarged cross-sectional view of FIG. 8 of the substrate assembly before pressing.
Figure 10:
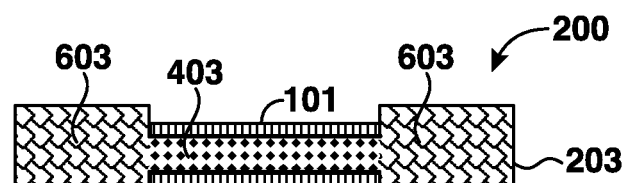
FIG. 10 provides the enlarged cross-sectional view of FIG. 9 after selective pressing of the electrodes showing both electrodes counter-sunk into the substrate to create sponge reservoirs.

To form the fuel cell of FIGS. 8-11, electrolyte layers (101) (generally of platinum and that are of similar construction) are placed upon opposing sides of a substrate (203). The electrolyte layers will generally be parallel mirrored electrode layers (101), but this is by no means required. These electrode (101) layers are smaller than the substrate material (203) and do not cover the entire substrate (203) surface (215) they are upon. In this case, the depicted electrodes (101) are about 15 mm diameter circles about 0.5 mm or less thick as shown in FIG. 8. The electrodes (101) are then selectively compressed with pressure applied over the area of the electrodes (101) but generally not substantially beyond it. This adheres the electrode (101) to the substrate (203) and permanently deforms the pore size in this selective area (403) of the substrate (203) which is between this electrodes (101). However, as can be seen in FIG. 10, the pressure is not supplied to the surrounding substrate (603) where the electrodes (101) are not present. Thus, the electrodes (101) end up "counter-sunk" into the center of the substrate (203).

It should be noted that the overall substrate (203) size (in this case about 25 mm square) is not critical to the invention nor is the shape. Likewise, the size and shape of the electrode (101) area is not critical to the invention. The exact proportion of electrode (101) compared to the rest of the substrate (603) that serves as an extra reservoir is also not critical to the invention. It only matters that the electrode (101) have a smaller surface area than the substrate (203).

Figure 11:
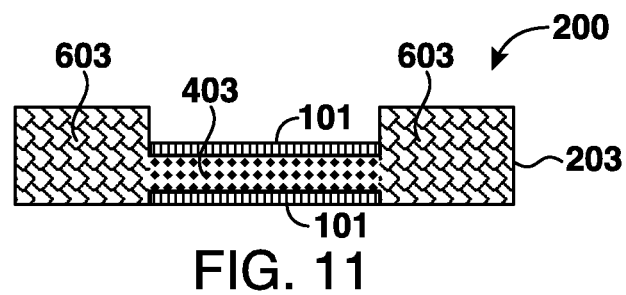
FIG. 11 provides the enlarged cross-sectional view of FIG. 9 after selective pressing of the electrodes showing the electrodes being off-center with only a single electrode counter-sunk into the substrate to create sponge reservoirs.

Further, the symmetry of the thickness of the compressed electrode portion (403) within the thickness of the overall non-compressed portion (603) is not critical to the invention and in different embodiments, such as is shown in FIG. 11, the electrodes (101) may be counter-sunk into the substrate (203) in differing amounts, including not having one of the electrodes (101) counter-sunk at all. This modification can be used to allow for alternative wire connections to the electrodes (101) as would be understood by one of ordinary skill in the art.

Figure 12A:
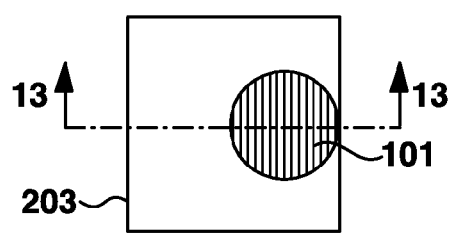
FIGS. 12A and 12B provides planar top views of two embodiments of electrodes selectively applied off-center on the substrate.
Figure 12B:
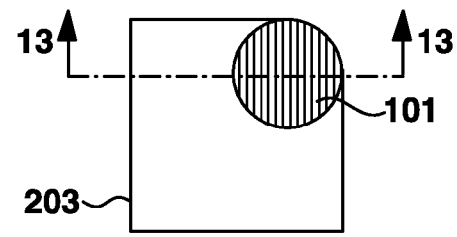
Figure 13:
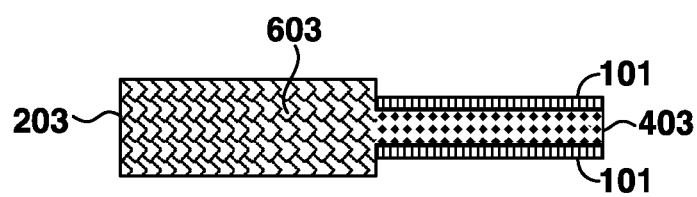
FIG. 13 provides an enlarged cross-sectional view of either embodiment of FIG. 12A or 12B after the selective pressing to create sponge reservoirs.

A further embodiment is shown by example in FIGS. 12A, 12B, and 13. In these FIGS, the selective pressing portion (403) (and thus the electrode (101)) is not required to be in the center of the non-compressed portion (603) of the single substrate (203). There might be reasons to move the selectively pressed portion (403) to the edge of the part, for example, to better facilitate how wires in contact with the electrodes (101) exit the case as they do not need to pass over the uncompressed portion (603) and can therefore be shorter. The non-centered compressed portion (403) could result in a design where only a portion of the entire perimeter edge of the compressed area (403) is in contact with non-compressed portions (603) and the remainder is exposed to air.

Figure 14:
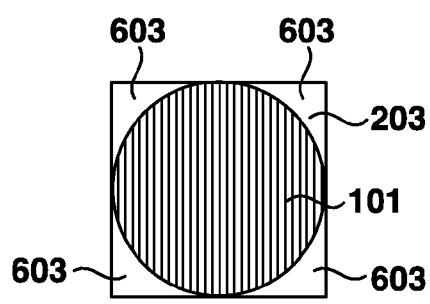
FIG. 14 provides a planar top view of another embodiment of an electrode assembly where the electrode is a circle with a diameter equal to the length of each side of the substrate.
Figure 15:
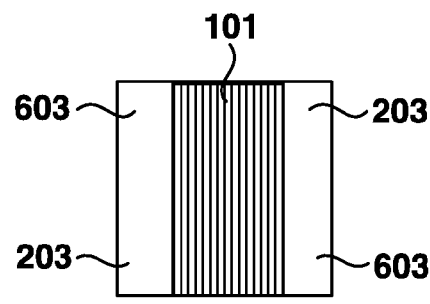
FIG. 15 provides a planar top view of another embodiment of an electrode assembly where the electrode is a rectangle with a long dimension equal to the length of each side of a square substrate.

FIGS. 14 and 15 provide for two more alternative embodiments of a fuel cell. In these embodiments the electrodes (101) are sized so as to share a single dimensional length with the substrate, but are not the same size and shape. Thus, the electrodes (101) will generally be arranged at an edge of the substrate (203) (generally at two opposing edges) but are not the same size and therefore, when the electrodes (101) are compressed, a portion (603) of the substrate (203) is still not compressed and acts as a sponge reservoir (603). In this type of arrangement, there will generally be two or more separate reservoirs (603) as the compressed portion (403) will act to separate the reservoirs (603).

As would be apparent to one of ordinary skill, all of the above variations are within the discretion of the designer depending on the sum of all the factors that influence the fuel cell sensor (200) design. There may be numerous variations along these lines without changing the nature of the invention.

In a still further embodiment, the fuel cell (200) is placed within a case (400) which serves to further enhance access to liquid electrolyte. Specifically, there may be included one or more liquid reservoirs (401) that work with or in conjunction with the sponge reservoir (603) formed from the substrate (203). Thus, there can be additional liquid electrolyte (401) that is in contact with the sponge reservoir (603). An embodiment of such a case (400), with a fuel cell (201) therein, is provided in FIGS. 16 and 17. The liquid reservoirs (401) in this embodiment (there are 6) are part of the case (400) design and are analogous to a bottle of liquid electrolyte which is in fluid contact with the sponge reservoir (603), whereas the sponge reservoir (603) in the electrode discussed above is more analogous to a storage sponge and is in integral fluid communication with the compressed substrate (403).

This aspect opens up the possibility of an easily refillable dual reservoir (sponge and liquid) system which could be monitored in various ways. By capillary action, the sponge reservoir (603) would generally continuously take in liquid from the liquid reservoir (401) as needed to replenish any loss. Thus, the sponge reservoir (603) would remain continuously full or at least full enough to supply the compressed substrate (403) so that it is always full even as the level of liquid in the liquid reservoirs (401) was depleted.

Figure 16:
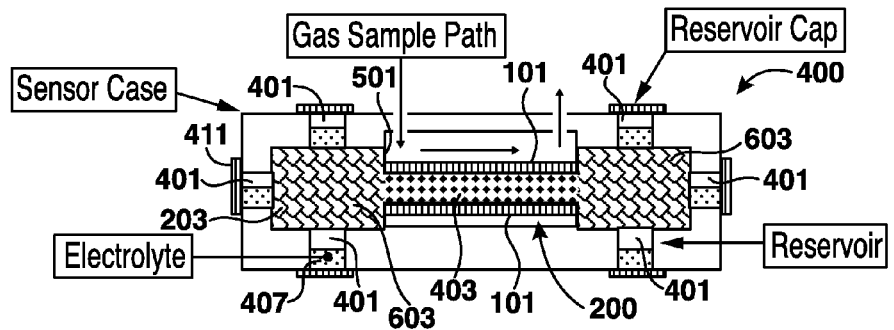
FIG. 16 provides a cross-sectional side view of a sensor of FIG. 10 inside a fuel cell case with six liquid or "bottle" reservoirs.
Figure 17:
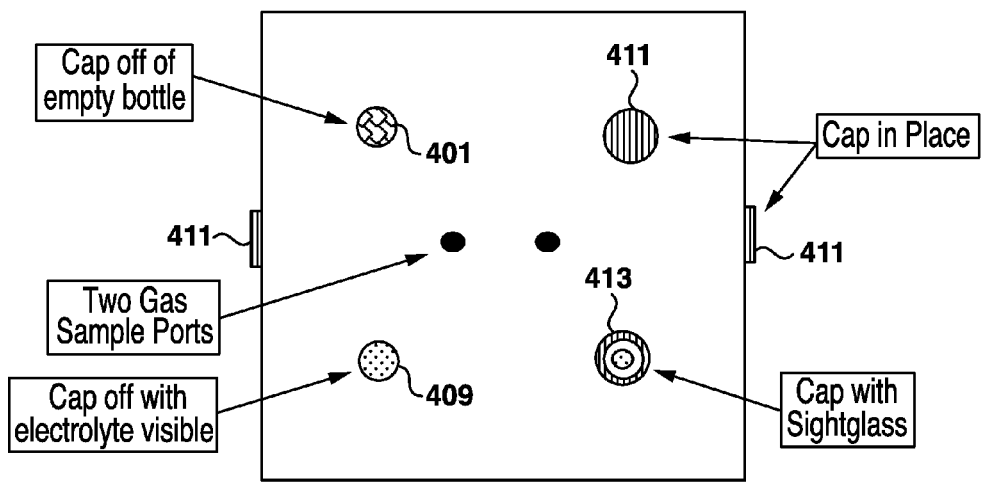
FIG. 17 provides a top view of a fuel cell case of FIG. 16 showing various caps and states of the various liquid reservoirs.

In order to provide liquid reservoirs (401), there could be a single "bottle" or there could be multiple "bottles" as shown in FIGS. 16-17. There could be "bottle(s)" on one side of the sponge reservoir (603) or multiple sides. In the event that the device was arranged so that there are multiple separated sponge reservoirs (603) (such as in FIGS. 14 and 15), each could have its own bottle (or bottles) or only certain sponge reservoirs (603) could include a bottle. Bottle(s) could be at the outer periphery of the sponge reservoirs (603), i.e., in contact with the edge of the sponge or along any surface including interior surfaces above the electrode (101) or even within the structure of the sponge reservoirs (603). Having bottles in multiple locations as is shown in FIGS. 16-17 allows replenishment of the sponge reservoir (603) no matter the orientation of the sensor (200) and/or measuring instrument. In effect, electrolyte (409) will be pulled by gravity to be in contact with the sponge reservoir (603) regardless of orientation.

Figure 1:
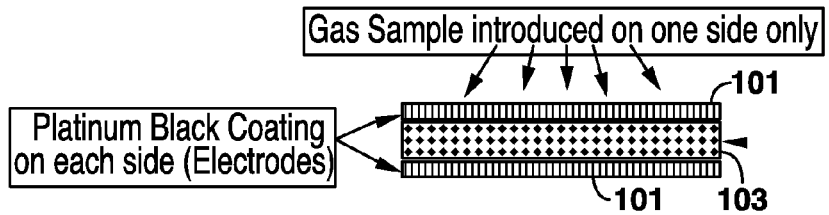
FIG. 1 shows an embodiment of a typical fuel cell of the prior art.
Figure 2:
FIG. 2. shows two embodiments of typical electrode shapes and sizes found in the prior art.
Figure 3:
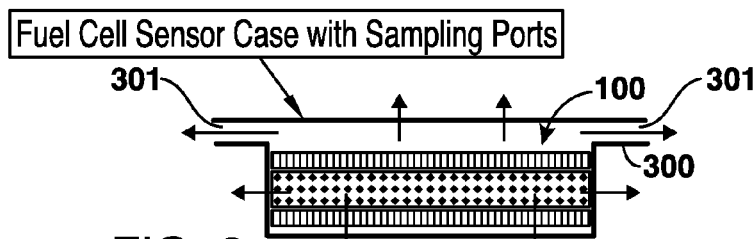
FIG. 3 shows various paths of liquid electrolyte water loss from a typical fuel cell including through sampling ports and a case body as found in the prior art.
Figure 4:
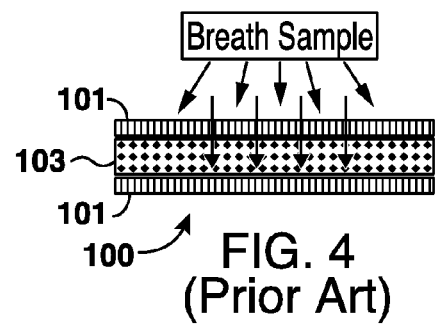
FIG. 4 shows potential recuperation of electrolyte water from humid breath samples of the prior art.
Figure 5:
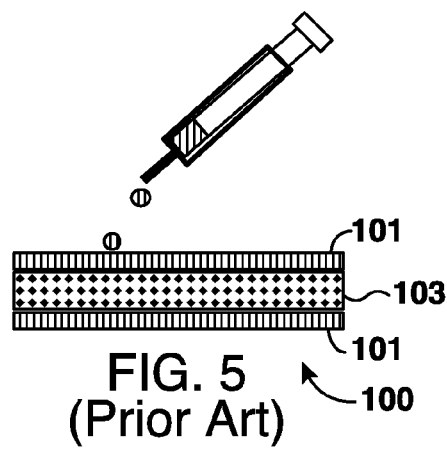
FIG. 5 shows a conceptual diagram of externally adding water to a fuel cell sensor of the prior art.
Figure 6:
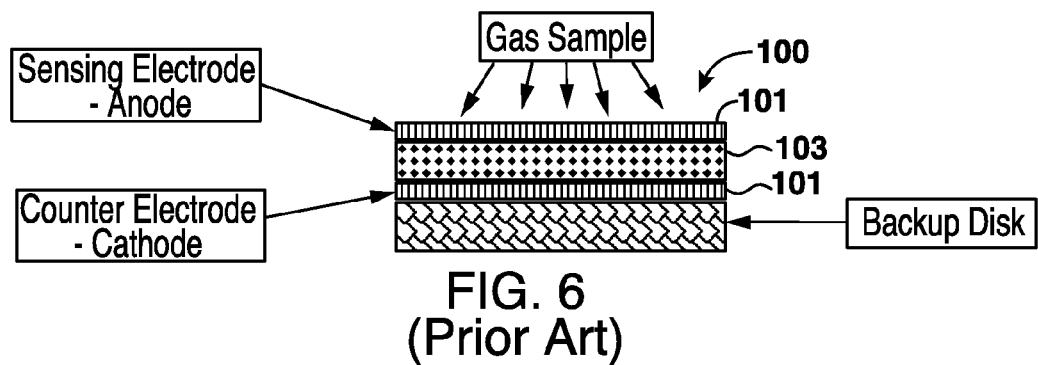
FIG. 6 shows an embodiment of a fuel cell sensor of the prior art with a backup substrate disk showing the capillary action taking electrolyte from the backup disk to the substrate.
Figure 7:
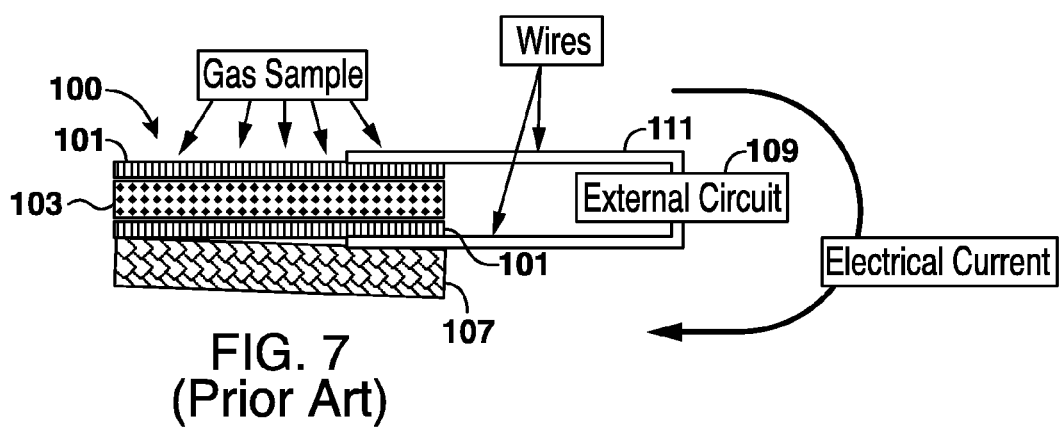
FIG. 7 shows an embodiment of a fuel cell sensor of the prior art with a backup disk showing the wires for the electrodes creating an imperfect connection with the backup disk.

In the embodiment of FIGS. 16 and 17, the case (400) is constructed such that there is no bottom to the liquid reservoir (401). Instead, the sponge reservoir (603) serves as the bottom. It is highly undesirable for liquid electrolyte to contact the electrode (101) surface on the gas sample side of the electrode, as this will severely degrade the ability of the sensor to accurately measure any gas sample unless it is removed prior to taking a sample. Because of this, it may be necessary to seal off all or a portion of the sponge reservoir (603) surface from the exterior or from the electrode (101). For example, surface (501) of the sponge reservoir (603) near the electrode (101) may be sealed in any manner understood from one of ordinary skill in the art to inhibit the sponge reservoir (603) from becoming overfilled and potentially "weeping" electrolyte onto the electrode (101) surface. In a still further embodiment, the capillary action of the sponge reservoir (603), if it was not full, can actually be used to pull liquid electrolyte from the electrode surface (101) to replenish its stock of electrolyte by allowing electrolyte to be placed on the electrode surface (101) as shown in FIG. 5 and then tilting the device of FIG. 16 to place surface (501) downward. Still further, the sponge action could similarly be used to pull fluid water or other fluids from the surface of the electrode (101).

Those skilled in the art will understand that the liquid reservoir(s) (401) can include caps (411) which could be removable for re-filling or not removable for a one-time fill. The caps (411) may, in an embodiment, be vented. Those skilled in the art will also understand that sensors of various types could be incorporated with the liquid reservoirs (401) and/or caps (411) to either visually or electronically monitor how full the liquid reservoirs (401) are, such as is shown in FIG. 17. Examples of such sensors could be a sight glass (413) or an electronic liquid level sensor. A single liquid reservoir (401) could hold many times the amount of electrolyte (409) held in the sponge reservoir (603) providing a large excess of electrolyte (409), but the exact amounts and proportions are at the discretion of the designer implementing the invention.

Those skilled in the art will understand the liquid reservoir (401) can be any shape and cover any amount of the sponge reservoir (603) surface. For example, a single liquid reservoir (401) could completely surround the entire edge perimeter of the sponge reservoir (603) as long as the electrolyte is maintained in the liquid reservoir (401) bottle or will enter the sponge reservoir (603). Alternatively, the sponge reservoir (603) can be used alone without the liquid reservoir (401). Conversely, an alternate embodiment of the invention has the liquid reservoir (401) only, attaching directly to the compressed substrate (403) of the active element.

Often, there is a desire to keep a fuel cell sensor (200) small such as in portable equipment. Although the selective pressing outlined above makes for a very compact design, there may be a desire to have a reservoir that could hold even more electrolyte without increasing the size by including liquid reservoirs (401) in the housing or case (400). In an embodiment of such an active element, additional electrolyte storage can be accomplished by the choice of material used for the substrate, depending on the nature of its pores in the compressed and uncompressed states, but differences in total reservoir volume with such design options may be marginal and may present other concerns.

Figure 18:
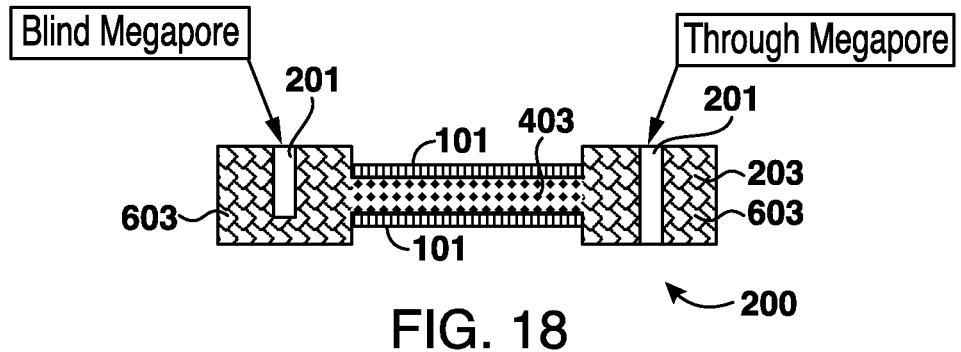
FIG. 18 provides an enlarged cross-sectional view of a fuel cell similar to that of FIG. 10. However, the sponge reservoirs of FIG. 18 include two different embodiments of empty megapores.
Figure 19:
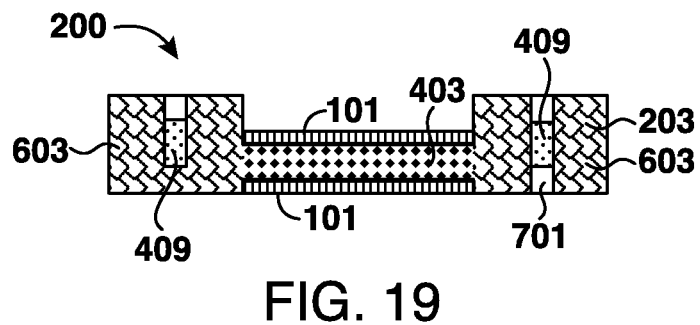
FIG. 19 provides an enlarged cross-sectional view of the fuel cell of FIG. 18 with partially full megapores.
Figure 20:
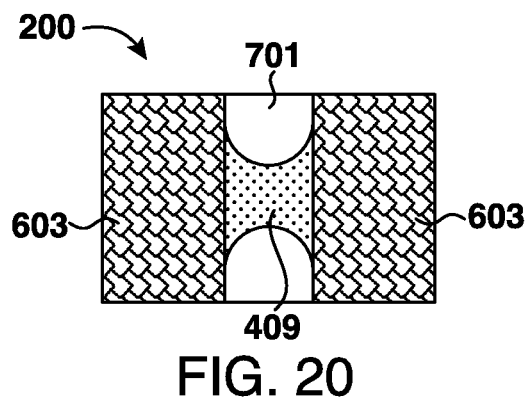
FIG. 20 provides an enlarged cross-sectional view of a megapore within a substrate, showing the result of capillary forces which can retain liquid in the megapore.

FIGS. 18-20 provide for a still further embodiment wherein the sponge reservoir (603) includes one or more megapores (701) in the uncompressed substrate (603) to act as small containers of liquid. In alternative embodiments, the megapore (701) may extend into, or be entirely within, the compressed portion (403). The size of the megapores (701) may vary, but will generally be limited so that capillary forces keep any liquid electrolyte (409) in the megapore (701) contained as shown in FIG. 20. In an embodiment, the megapores (701) are empty when the sensor (200) is brand new, with the remaining substrate (203) saturated with electrolyte. In this case, the megapore (701) is strictly to handle overflow in a controlled manner if the sensor (200) takes on excess water. This can occur if the device including the fuel cell (200) is to be used in particularly humid locations or in applications which may require its immersion in fluid. In another embodiment, the megapore (701) is partially filled (as shown in FIG. 19) to provide for an alternative liquid reservoir, but still contains some available volume for overflow. As shown in FIG. 18, the megapores (701) can be through-holes in the substrate (203) or blind holes in the substrate (203). They may be formed as part of the substrate (203) formation, or may be added later, such as, but not limited to, by drilling. In an embodiment, the megapores (701) could also have caps (411).

While the invention has been disclosed in connection with certain preferred embodiments, this should not be taken as a limitation to all of the provided details. Modifications and variations of the described embodiments may be made without departing from the spirit and scope of the invention, and other embodiments should be understood to be encompassed in the present disclosure as would be understood by those of ordinary skill in the art.

The invention claimed is:

1. A method of forming a fuel cell, the method comprising:
    placing a first electrode on a first side of a substrate, said first electrode covering only a portion of said first side;
    placing a second electrode on a second opposing side of a substrate, said second electrode covering only a portion of said second side;
    moving said first electrode and said second electrode toward each other so as to compress said substrate located between said first electrode and said second electrode while not compressing said substrate not located between said first electrode and said second electrode.

2. The method of claim 1 wherein said moving comprises moving both said first electrode and said second electrode.

3. The method of claim 1 wherein said moving comprises moving only one of said first electrode and said second electrode.

4. The method of claim 1 further comprising: encapsulating said fuel cell in a housing.

5. The method of claim 4 wherein said housing includes at least one liquid reservoir in fluid communication with said substrate not located between said first electrode and said second electrode.

6. The method of claim 5 wherein said at least one liquid reservoir comprises at least three liquid reservoirs, said at least three liquid reservoirs being positioned so that liquid in at least one of said at least three reservoirs contacts said substrate not located between said first electrode and said second electrode regardless of orientation of said fuel cell.

7. The method of claim 1 wherein said electrodes comprise platinum.

8. The method of claim 1 further comprising: placing said fuel cell in a breath alcohol sensor.

9. The method of claim 1 wherein said substrate comprises porous polypropylene.

10. The method of claim 1 wherein said substrate comprises porous polyvinylchloride (PVC).

11. The method of claim 1 wherein pores in said substrate include a liquid electrolyte.

12. The method of claim 1 wherein said electrodes are circular.

13. The method of claim 1 wherein said substrate is polygonal.

14. The method of claim 1 wherein said substrate located between said first electrode and said second electrode includes a megapore.

15. The method of claim 1 wherein said substrate not located between said first electrode and said second electrode includes a megapore.

* * * * *